(12) United States Patent
de la Rama et al.

(10) Patent No.: US 10,362,954 B2
(45) Date of Patent: Jul. 30, 2019

(54) HIGH DENSITY ELECTRODE MAPPING CATHETER

(71) Applicant: St. Jude Medical, Cardiology Division, Inc., St. Paul, MN (US)

(72) Inventors: Alan de la Rama, Cerritos, CA (US); Cary Hata, Irvine, CA (US); Tim La, Santa Ana, CA (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 310 days.

(21) Appl. No.: 15/331,369

(22) Filed: Oct. 21, 2016

(65) Prior Publication Data

US 2017/0112404 A1    Apr. 27, 2017

Related U.S. Application Data

(60) Provisional application No. 62/244,630, filed on Oct. 21, 2015.

(51) Int. Cl.
*A61B 5/04* (2006.01)
*A61B 5/042* (2006.01)
(Continued)

(52) U.S. Cl.
CPC .......... *A61B 5/0422* (2013.01); *A61B 5/6852* (2013.01); *A61B 5/6858* (2013.01);
(Continued)

(58) Field of Classification Search
CPC .......... A61B 2018/0016; A61B 5/0422; A61B 5/04286; A61B 5/04085; A61B 5/04;
(Continued)

(56) References Cited

U.S. PATENT DOCUMENTS 5,465,717 A    11/1995  Imran et al.
6,071,282 A *  6/2000  Fleischman ........ A61B 18/1492
                                                    600/374

(Continued)

FOREIGN PATENT DOCUMENTS

WO    2005/114720 A2    12/2005
WO    2008/157399 A1    12/2008
WO    2014/113612 A1    7/2014

OTHER PUBLICATIONS

Rao, Chepuri R.K. and Trivedi, D.C., Chemical and electrochemical depositions of platinum group metals and their applications, Coordination Chemistry Reviews, 249, (2005) pp. 613-631.

(Continued)

*Primary Examiner* — Eun Hwa Kim
(74) *Attorney, Agent, or Firm* — Dykema Gossett PLLC

(57) ABSTRACT

Various embodiments of the present disclosure can include a flexible catheter tip. The flexible catheter tip can comprise an inboard understructure that defines a tip longitudinal axis, wherein the inboard understructure is formed from a first continuous element that includes a first rectangular cross-section. In some embodiments, an outboard understructure can extend along the tip longitudinal axis, wherein the outboard understructure is formed from a second continuous element that includes a second rectangular cross-section.

15 Claims, 14 Drawing Sheets

(51) Int. Cl.
*A61B 5/00* (2006.01)
*A61B 18/14* (2006.01)
*A61B 18/00* (2006.01)

(52) U.S. Cl.
CPC ............... *A61B 18/1492* (2013.01); *A61B 2018/00267* (2013.01); *A61B 2018/00357* (2013.01); *A61B 2018/00577* (2013.01); *A61B 2018/00839* (2013.01)

(58) Field of Classification Search
CPC . A61B 5/6858; A61B 5/6852; A61B 18/1492; A61B 2018/00839; A61B 2018/00267
See application file for complete search history.

(56) References Cited

U.S. PATENT DOCUMENTS

| | | | |
|---|---|---|---|
| 8,103,327 | B2 | 1/2012 | Harlev et al. |
| 8,364,234 | B2 | 1/2013 | Kordis et al. |
| 8,560,086 | B2 | 10/2013 | Just et al. |
| 8,795,504 | B2 | 8/2014 | Petrossians et al. |
| 2008/0312521 | A1 | 12/2008 | Solomon |
| 2014/0142408 | A1 | 5/2014 | de la Rama et al. |
| 2014/0288552 | A1 | 9/2014 | Kunis et al. |

OTHER PUBLICATIONS

Sheela G., et al., Electrodeposition of Iridium, Bulletin of Electrochemistry, 15 (5-6) May-Jun. 1999, pp. 208-210.
WU, Feng, et al., Electrodeposition of Platinum-Iridium Alloy on Nickel-Base Single-Crystal Superalloy TMS75, Surface and Coatings Technology vol. 184, Issue 1, Jun. 1, 2004.
Baumgartner, M.E. and Raub, CH. J., The Electrodeposition of Platinum and Platinum Alloys, Platinum Metals Review, 1988, 32, (4), 188-197.
Ohno, Izumi, Electroless Deposition of Palladium and Platinum, Modern Electroplating, 5th Edition, Edited by Mordechay Schlesinger and Milan Paunovic, Copyright 2010, John Wiley & Sons, Inc. Chp 20, 477-482.
Electroplating the Platinum Metals—A Recent Survey of Processes and Applications, Platinum Metals Rev., 1970, 14, (3) pp. 93-94.
Yingna Wu et al., Characterization of Electroplated Platinum-Iridium Alloys on the Nickel-Base Single Crystal Superalloy, Materials Transactions, vol. 46, No. 10 (2005) pp. 2176-2179.

* cited by examiner

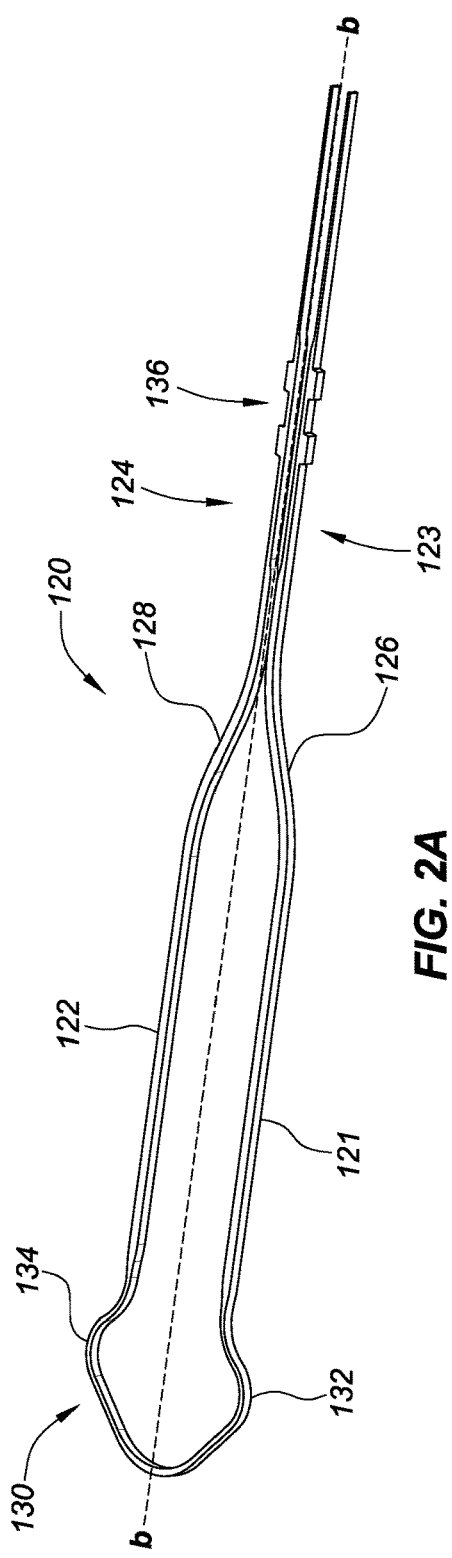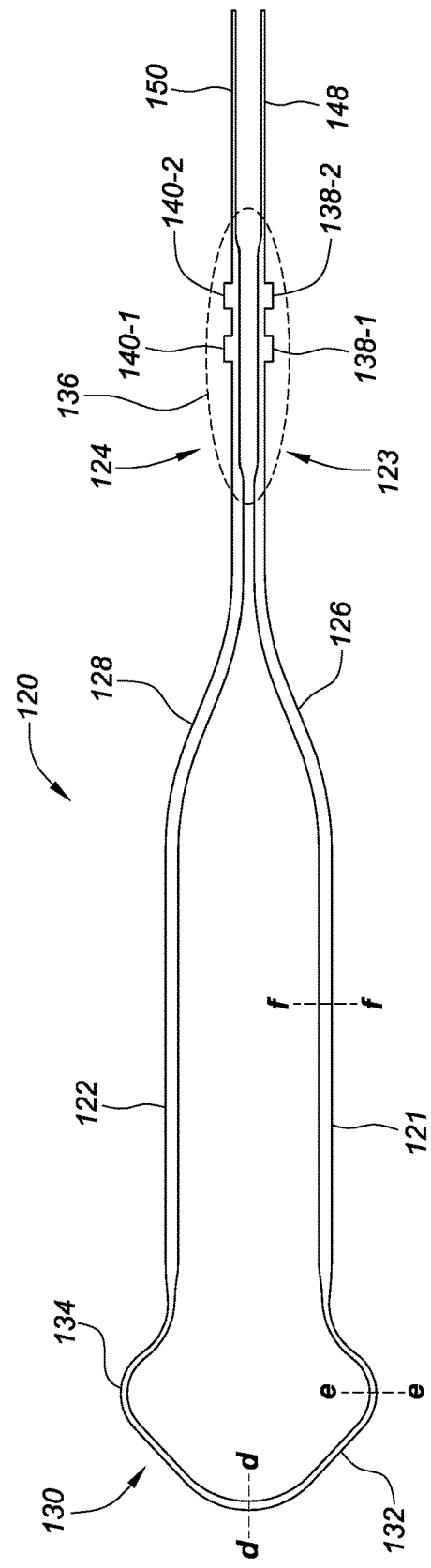
FIG. 2A
FIG. 2B

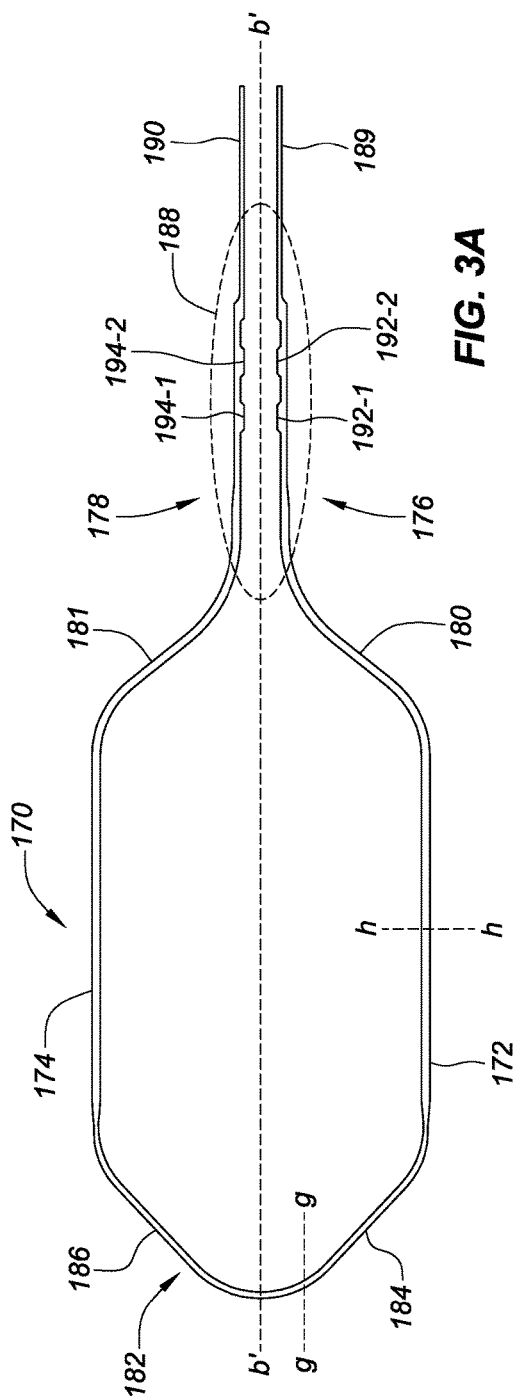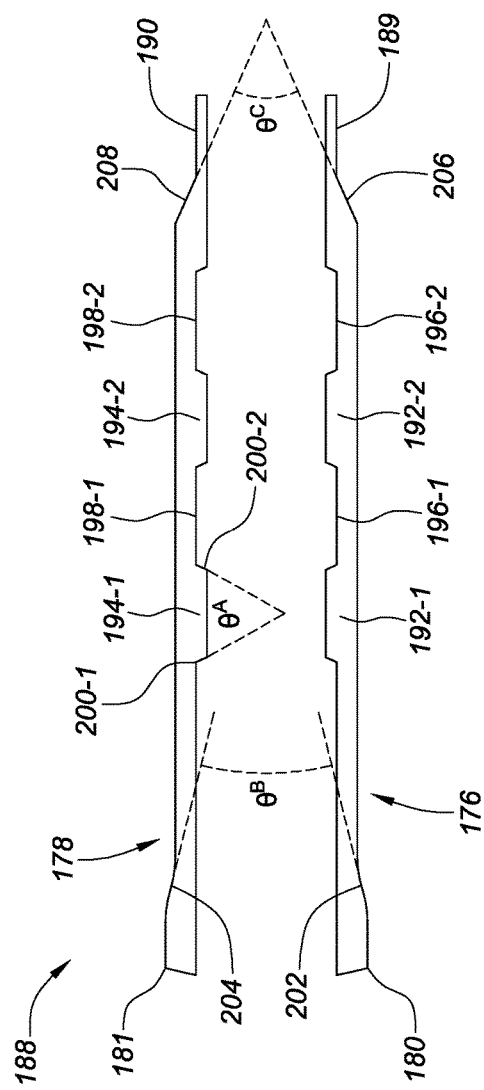

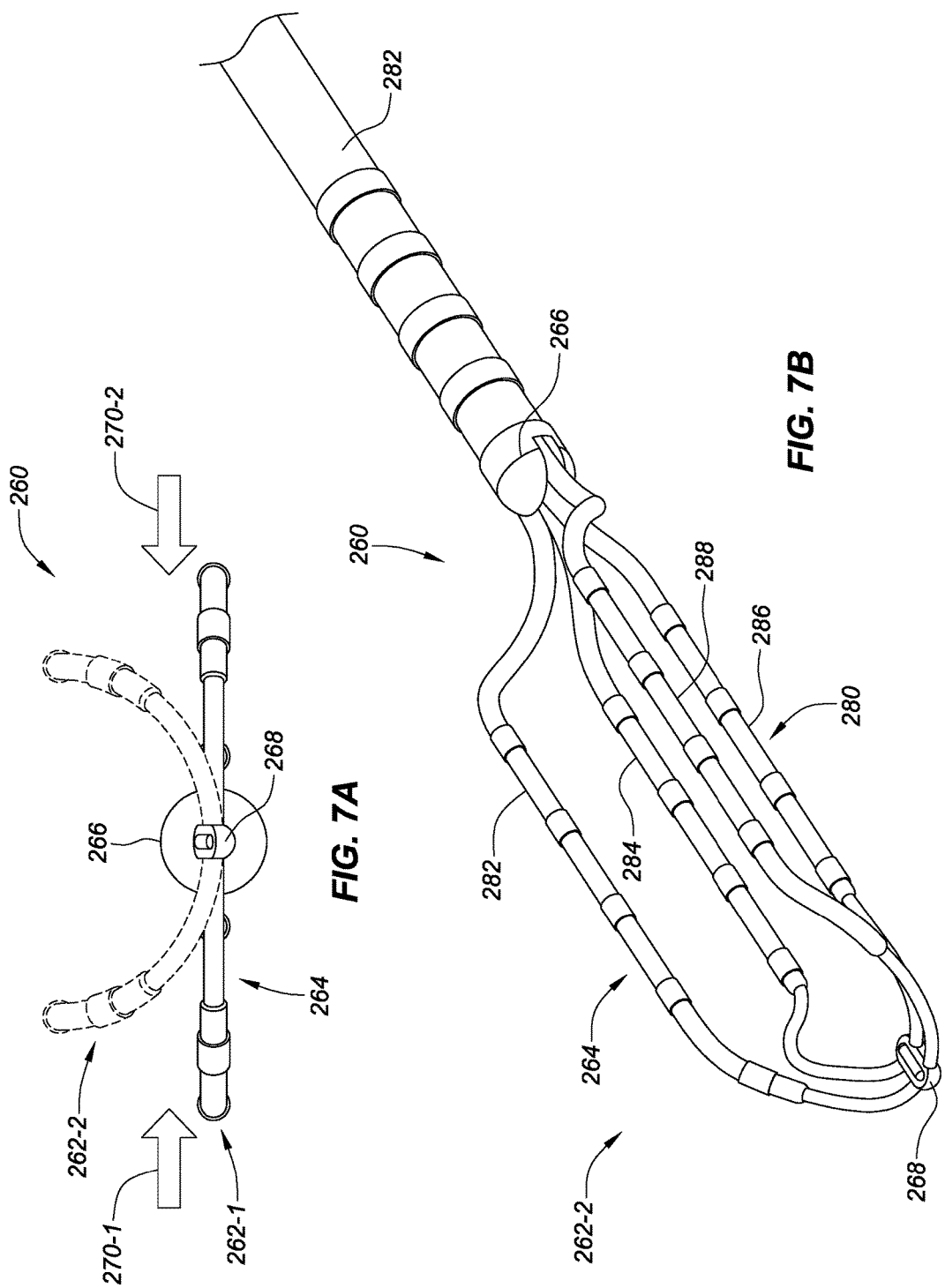

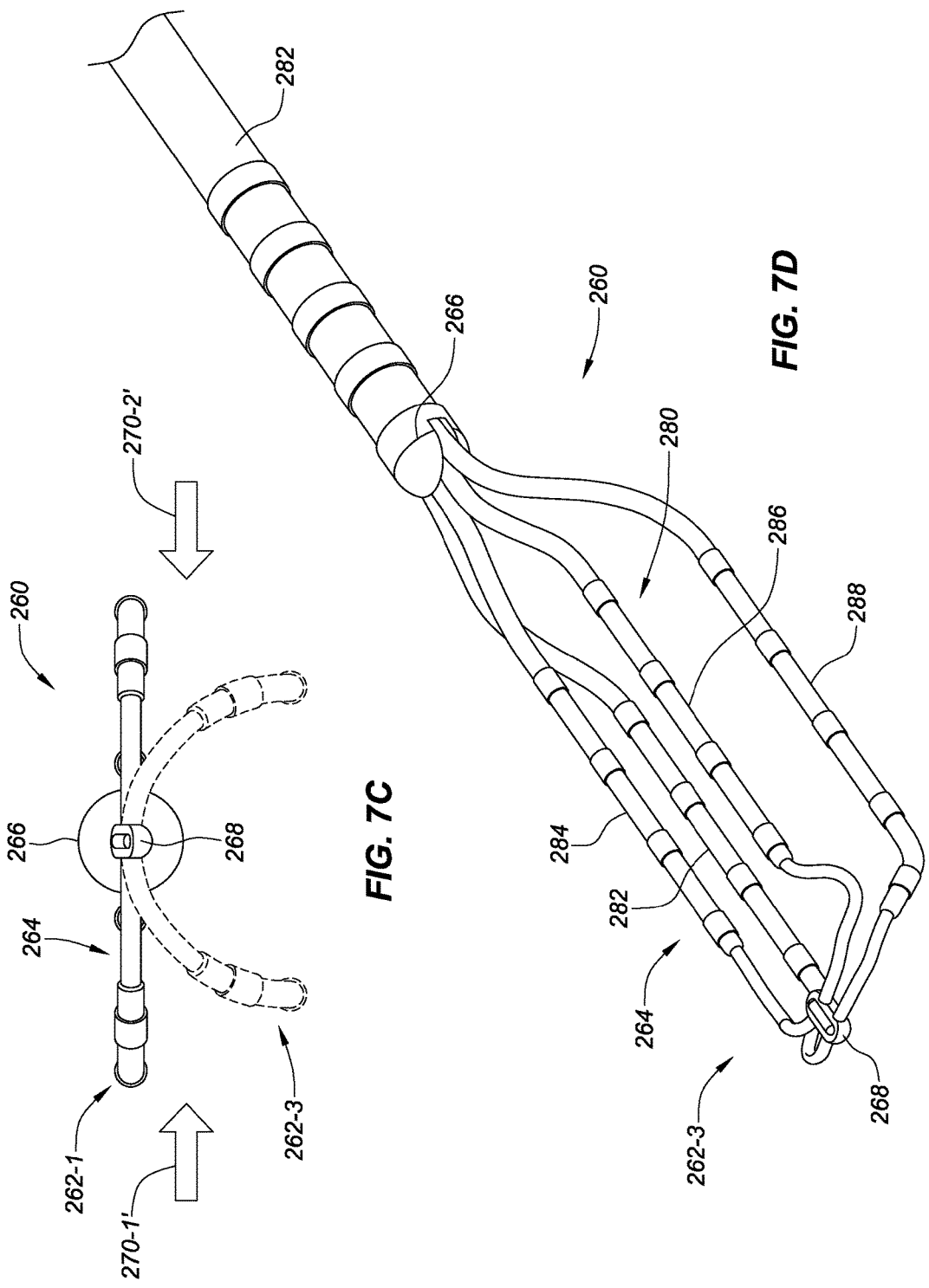

HIGH DENSITY ELECTRODE MAPPING CATHETER

CROSS-REFERENCE TO RELATED APPLICATION

This application claims priority to U.S. provisional application No. 62/244,630, filed 21 Oct. 2015, which is hereby incorporated by reference as though fully set forth herein. This application is related to U.S. application Ser. No. 15/331,562, filed 21 Oct. 2016, which is hereby incorporated by reference as though fully set forth herein.

FIELD OF THE DISCLOSURE

This disclosure relates to a high density electrode mapping catheter.

BACKGROUND ART

Catheters have been used for cardiac medical procedures for many years. Catheters can be used, for example, to diagnose and treat cardiac arrhythmias, while positioned at a specific location within a body that is otherwise inaccessible without a more invasive procedure.

Conventional mapping catheters may include, for example, a plurality of adjacent ring electrodes encircling the longitudinal axis of the catheter and constructed from platinum or some other metal. These ring electrodes are relatively rigid. Similarly, conventional ablation catheters may comprise a relatively rigid tip electrode for delivering therapy (e.g., delivering RF ablation energy) and may also include a plurality of adjacent ring electrodes. It can be difficult to maintain good electrical contact with cardiac tissue when using these conventional catheters and their relatively rigid (or nonconforming), metallic electrodes, especially when sharp gradients and undulations are present.

Whether mapping or forming lesions in a heart, the beating of the heart, especially if erratic or irregular, complicates matters, making it difficult to keep adequate contact between electrodes and tissue for a sufficient length of time. These problems are exacerbated on contoured or trabeculated surfaces. If the contact between the electrodes and the tissue cannot be sufficiently maintained, quality lesions or accurate mapping are unlikely to result.

The foregoing discussion is intended only to illustrate the present field and should not be taken as a disavowal of claim scope.

BRIEF SUMMARY

Various embodiments of the present disclosure can include a flexible catheter tip. The flexible catheter tip can comprise an inboard understructure that defines a tip longitudinal axis, wherein the inboard understructure is formed from a first continuous element that includes a first rectangular cross-section. In some embodiments, an outboard understructure can extend along the tip longitudinal axis, wherein the outboard understructure is formed from a second continuous element that includes a second rectangular cross-section.

Various embodiments of the present disclosure can include an integrated electrode structure. The integrated electrode structure can comprise a catheter shaft that includes a proximal end and a distal end, the catheter shaft defining a catheter shaft longitudinal axis. A flexible tip portion can be located adjacent to the distal end of the catheter shaft. The flexible tip portion can comprise a flexible framework that includes an inboard understructure. The inboard understructure can comprise a first continuous element that includes a first rectangular cross-section that extends along the shaft longitudinal axis; an outboard understructure, the outboard understructure including a second continuous element that includes a second rectangular cross-section that extends along the shaft longitudinal axis; and a distal coupler that connects a distal end of the inboard understructure and a distal end of the outboard understructure.

Various embodiments of the present disclosure can include a medical device. The medical device can comprise a catheter shaft that includes a proximal end and a distal end, the catheter shaft defining a catheter shaft longitudinal axis. The medical device can comprise a flexible tip portion, the flexible tip portion comprising a flexible framework that includes an inboard understructure, the inboard understructure including a pair of proximal inboard mounting arms mounted in the distal end of the catheter shaft, wherein each of the proximal inboard mounting arms include an inboard frame lock portion; and an outboard understructure, the outboard understructure including a pair of proximal outboard mounting arms mounted in the distal end of the catheter shaft, wherein each of the proximal outboard mounting arms include an outboard frame lock portion that corresponds with the inboard frame lock portion.

BRIEF DESCRIPTION OF THE DRAWINGS

FIG. 2A is an isometric side and top view of an inboard understructure of a high density electrode mapping catheter in FIG. 1A, according to various embodiments of the present disclosure.

FIG. 2B is a top view of the inboard understructure depicted in FIG. 2A, according to various embodiments of the present disclosure.

FIG. 3A is a top view of an outboard understructure of a high density electrode mapping catheter depicted in FIG. 1A, according to various embodiments of the present disclosure.

FIG. 3B is an enlarged view of an outboard frame lock portion of the outboard understructure depicted in FIG. 3A, according to various embodiments of the present disclosure.

FIG. 7A is a front view of a high density electrode mapping catheter in a first deflection state and a second deflection state, according to various embodiments of the present disclosure.

FIG. 7B is an isometric, side, front, and top view of the high density electrode mapping catheter in the second deflection state in FIG. 7A, according to various embodiments of the present disclosure.

FIG. 7C is a front view of the high density electrode mapping catheter depicted in FIGS. 7A and 7B in the first deflection state and a third deflection state, according to various embodiments of the present disclosure.

FIG. 7D is an isometric, side, front, and top view of the high density electrode mapping catheter in the third deflection state in FIG. 7C, according to various embodiments of the present disclosure.

DETAILED DESCRIPTION

The contents of International Application No. PCT/US2014/011940 entitled Flexible High-Density Mapping Catheter Tips and Flexible Ablation Catheter Tips with Onboard High-Density Mapping Electrodes is hereby incorporated by reference.

Figure 1A:
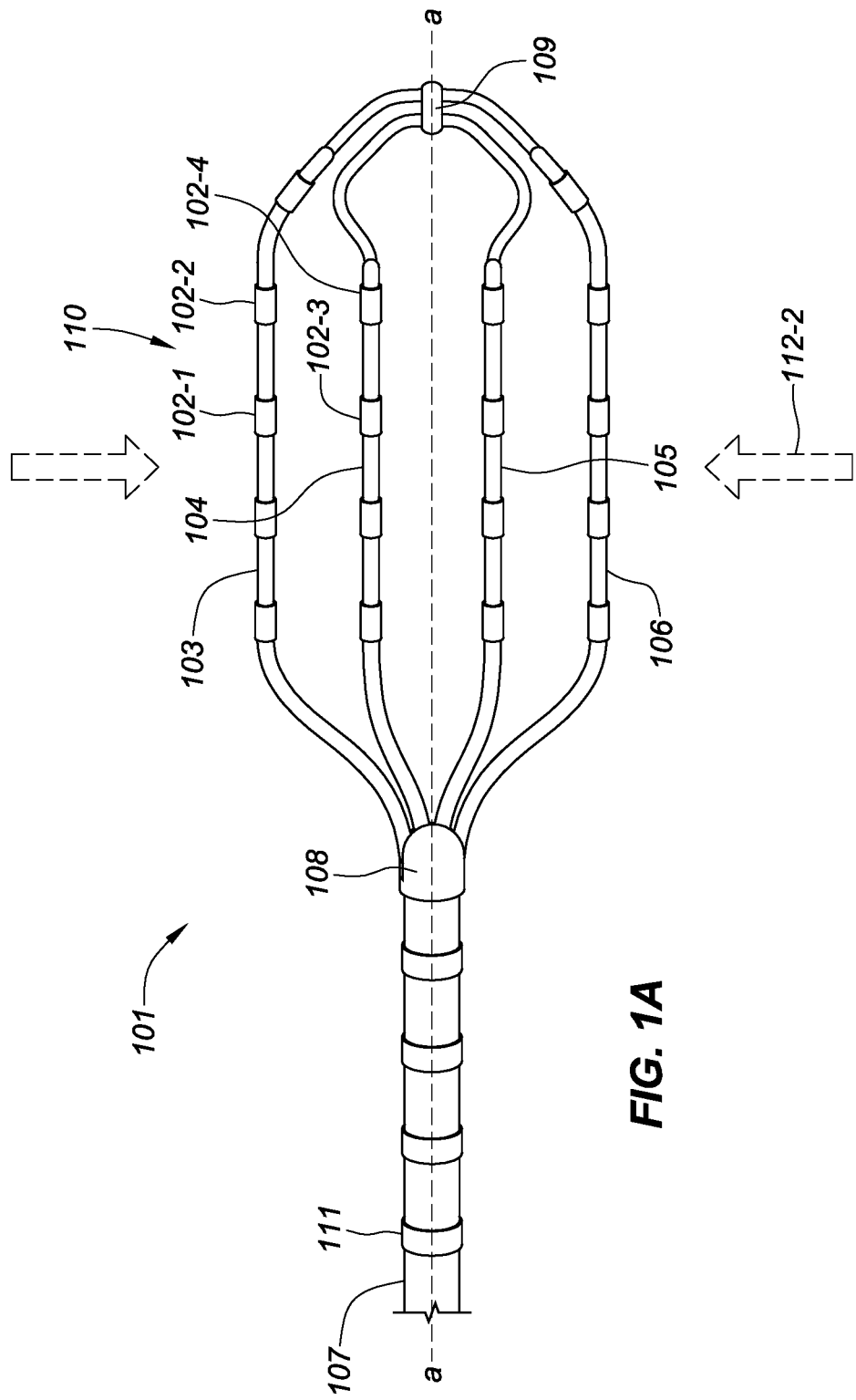
FIG. 1A is a top view of a high density electrode mapping catheter, according to various embodiments of the present disclosure.
Figure 1B:
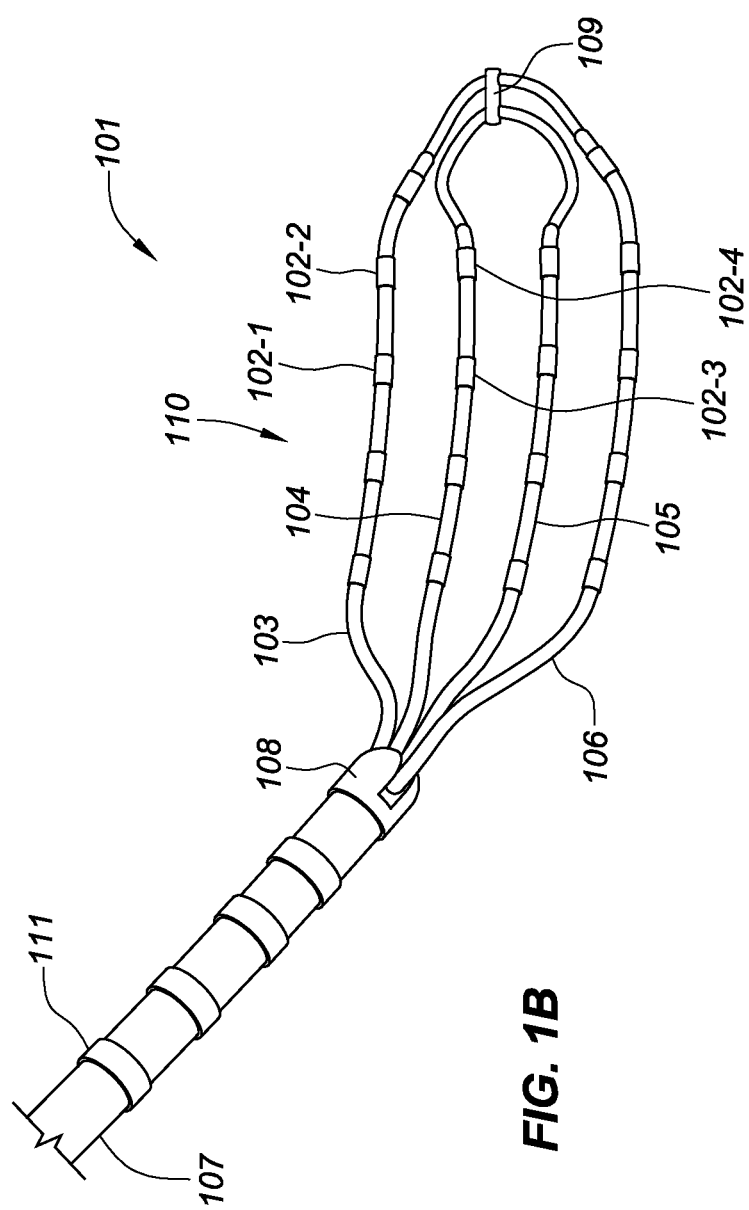
FIG. 1B is an isometric side and top view of the high density electrode mapping catheter in FIG. 1A, according to various embodiments of the present disclosure.

FIG. 1A is a top view of a high density electrode mapping catheter 101 and FIG. 1B is an isometric side and top view of the high density electrode mapping catheter 101, according to various embodiments of the present disclosure. In some embodiments, the high density electrode mapping catheter 101 can include a flexible tip portion 110 that forms a flexible array of microelectrodes 102-1, 102-2, 102-3, 102-4. Hereinafter, microelectrodes 102-1, 102-2, 102-3, 102-4 are referred to in the plural as microelectrodes 102. For ease of reference, only four microelectrodes 102 are labeled in FIG. 1A, however, the high density mapping catheter 101 can include more than four microelectrodes, as depicted. This planar array (or 'paddle' configuration) of microelectrodes 102 comprises four side-by-side, longitudinally-extending arms 103, 104, 105, 106, which can form a flexible framework on which the microelectrodes 102 are disposed. The four microelectrode-carrier arms comprise a first outboard arm 103, a second outboard arm 106, a first inboard arm 104, and a second inboard arm 105, which can be connected via a distal coupler 109. These arms can be laterally separated from each other.

Each of the four arms can carry a plurality of microelectrodes 102. For example, each of the four arms can carry microelectrodes 102 spaced along a length of each of the four arms. Although each of the high density electrode mapping catheters 101 depicted in FIGS. 1A and 1B depict four arms, the high density electrode mapping catheters 101 could comprise more or fewer arms. Additionally, while the high density electrode mapping catheter 101 depicted in FIGS. 1A and 1B is depicted as including 18 electrodes (e.g., 5 microelectrodes on first outboard arm 103 and second outboard arm 106 and 4 microelectrodes on first inboard arm 104 and second inboard arm 105), the catheters can include more or fewer than 18 electrodes. In addition, the first outboard arm 103 and second outboard arm 106 can include more or fewer than 5 microelectrodes and the first inboard arm 104 and second inboard arm 105 can include more or fewer than 4 microelectrodes).

In some embodiments, the microelectrodes 102 can be used in diagnostic, therapeutic, and/or mapping procedures. For example and without limitation, the microelectrodes 102 can be used for electrophysiological studies, pacing, cardiac mapping, and/or ablation. In some embodiments, the microelectrodes 102 can be used to perform unipolar or bipolar ablation. This unipolar or bipolar ablation can create specific lines or patterns of lesions. In some embodiments, the microelectrodes 102 can receive electrical signals from the heart, which can be used for electrophysiological studies. In some embodiments, the microelectrodes 102 can perform a location or position sensing function related to cardiac mapping.

In some embodiments, the high density electrode mapping catheter 101 can include a catheter shaft 107. The catheter shaft 107 can include a proximal end and a distal end. The distal end can include a connector 108, which can couple the distal end of the catheter shaft 107 to a proximal end of the planar array. The catheter shaft 107 can define a catheter shaft longitudinal axis aa, as depicted in FIG. 1A, along which the first outboard arm 103, first inboard arm 104, second inboard arm 105, and second outboard arm 106 can generally extend parallel in relation therewith. The catheter shaft 107 can be made of a flexible material, such that it can be threaded through a tortuous vasculature of a patient. In some embodiments, the catheter shaft 107 can include one or more ring electrodes 111 disposed along a length of the catheter shaft 107. The ring electrodes 111 can be used for diagnostic, therapeutic, and/or mapping procedures, in an example.

As depicted in FIG. 1B, the flexible tip portion 110 can be adapted to conform to tissue (e.g., cardiac tissue). For example, when the flexible tip portion 110 contacts tissue, the flexible tip portion 110 can deflect, allowing the flexible framework to conform to the tissue. In some embodiments, the arms (or the understructure of the arms) comprising the paddle structure (or multi-arm, electrode-carrying, flexible framework) at the distal end of the catheters depicted in FIGS. 1A and 1B can be laser cut from a flexible or spring-like material such as Nitinol and/or a flexible substrate, as discussed herein. In some embodiments, the arms (or the understructure of the arms) can be formed from a sheet of metal (e.g., Nitinol) with a uniform thickness. Different portions of the arms (or understructure of the arms)

can he formed from the sheet (e.g., cut) such that the different portions of the arms have varying widths. The construction (including, for example, the length and/or diameter of the arms) and material of the arms can be adjusted or tailored to he created, for example, desired resiliency, flexibility, foldability, conformability, and stiffness characteristics, including one or more characteristics that may vary from the proximal end of a single arm to the distal end of that arm, or between or among the plurality of arms comprising a single paddle structure. The foldability of materials such as Nitinol and/or another type of flexible substrate provide the additional advantage of facilitating insertion of the paddle structure into a delivery catheter or introducer, whether during delivery of the catheter into the body or removal of the catheter from the body at the end of a procedure.

Among other things, the disclosed catheters, with their plurality of microelectrodes, are useful to (1) define regional propagation maps of particularly sized areas (e.g., one centimeter square areas) within the atrial walls of the heart; (2) identify complex fractionated atrial electrograms for ablation; (3) identify localized, focal potentials between the microelectrodes for higher electrogram resolution; and/or (4) more precisely target areas for ablation. These mapping catheters and ablation catheters are constructed to conform to, and remain in contact with, cardiac tissue despite potentially erratic cardiac motion. Such enhanced stability of the catheter on a heart wall during cardiac motion provides more accurate mapping and ablation due to sustained tissue-electrode contact. Additionally, the catheters described herein may be useful for epicardial and/or endocardial use. For example, the planar array embodiments depicted herein may be used in an epicardial procedure where the planar array of microelectrodes is positioned between the myocardial surface and the pericardium. Alternatively the planar array embodiments may be used in an endocardial procedure to quickly sweep and/or analyze the inner surfaces of the myocardium and quickly create high-density maps of the heart tissue's electrical properties.

FIG. 2A is an isometric side and top view of an inboard understructure 120 (also referred to herein as inner understructure) of the high density electrode mapping catheter depicted in FIG. 1A, according to various embodiments of the present disclosure. In some embodiments, the inboard understructure 120 can be formed from a flexible or spring-like material such as Nitinol and/or a flexible substrate, as discussed herein. In an example, the inboard understructure can be cut from a planar sheet of material (e.g., planar substrate). The inboard understructure 120 can include a first inboard arm understructure 121 and a second inboard arm understructure 122. Although not shown, the outboard understructure (also referred to herein as outer understructure) that provides the understructure for the first outboard arm 103 and the second outboard arm 106 can be formed and/or processed in a manner analogous to that discussed in relation to the inboard understructure 120. Further, if the high density electrode mapping catheter includes additional arms, those arms can be formed and/or processed in a manner analogous to that discussed in relation to the inboard understructure 120. For the sake of brevity, discussion is directed towards the inboard understructure 120. As depicted, the inboard understructure 120 can include a first proximal inboard mounting arm 123 and a second proximal inboard mounting arm 124. The proximal inboard mounting arms can be inserted into a distal end of the catheter 107 and through the connector 108 and can be used to connect the flexible tip portion 110 to the distal end of the catheter 107.

In some embodiments, the proximal inboard mounting arms can be inserted through a torsional spacer, as discussed herein.

In some embodiments, the inboard understructure 120 can define a tip longitudinal axis, depicted by line bb. In some embodiments, the inboard understructure 120 can be formed from a continuous element that includes a first rectangular cross-section. As used herein, a rectangular cross-section can include a square cross-section. For example, the inboard understructure 120 can include the first proximal inboard mounting arm 123 and second proximal inboard mounting arm 124, which can extend along the longitudinal axis. The inboard understructure 120 can include a first inboard arm understructure 121 that extends distally from the first proximal inboard mounting arm 123 and can include a second inboard arm understructure 122 that extends distally from the second proximal inboard mounting arm 124. In some embodiments, the first inboard arm understructure 121 and the second inboard arm understructure 122 can extend parallel to the tip longitudinal axis bb and to one another.

In some embodiments, a first transition understructure portion 126 can be disposed between the first proximal inboard mounting arm 123 and the first inboard arm understructure 121. The first transition understructure portion 126 can be laterally flared away from the tip longitudinal axis bb. Additionally, a second transition understructure portion 127 can be disposed between the second proximal inboard mounting arm 124 and the second inboard arm understructure 122. The second transition understructure portion 128 can be laterally flared away from the tip longitudinal axis bb. In an example, the first transition understructure portion 126 and the second transition understructure portion 128 can be flared away from one another.

In some embodiments, the inboard understructure 120 includes a flared head portion 130 that is connected to distal ends of the first and second inboard arm understructures 121, 122. In some embodiments, the flared head portion 130 can be formed from a first flared element 132 and a second flared element 134. As the first flared element 132 and the second flared element 134 extend distally, the elements 132, 134 can be laterally flared away from the tip longitudinal axis bb and away from one another, before extending toward the tip longitudinal axis bb and toward one another. The first flared element 132 and the second flared element 134 can be connected along the tip longitudinal axis bb. In an example, the inboard understructure can be symmetrical along either side of the tip longitudinal axis bb.

In some embodiments, the proximal inboard portion of the inboard frame understructure 120 can include the first proximal inboard mounting arm 123 and the second proximal inboard mounting arm 124. In an example, the proximal inboard portion of the inboard frame understructure 120 can include an inboard frame lock portion 136, which is further discussed in relation to FIG. 2B.

Figure 2C:
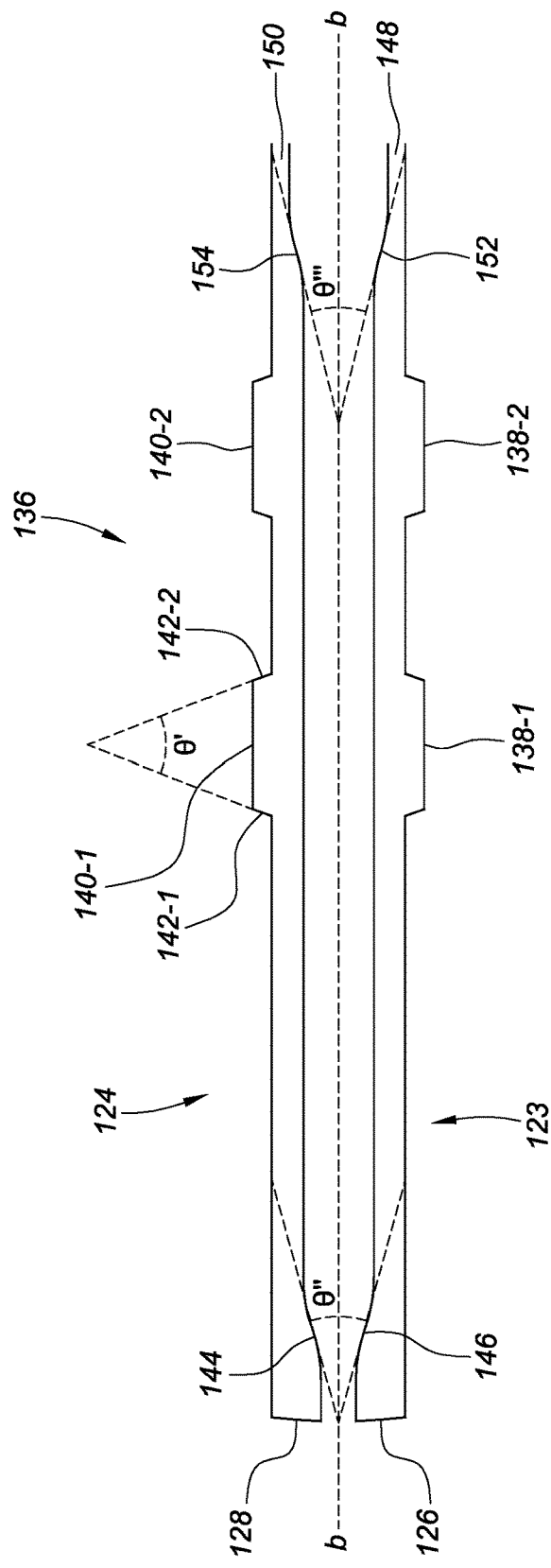
FIG. 2C is an enlarged view of an inboard frame lock portion of the inboard understructure depicted in FIG. 2A, according to various embodiments of the present disclosure.

FIG. 2B depicts a top view of the inboard understructure 120 depicted in FIG. 2A, according to various embodiments of the present disclosure. FIG. 2B depicts the inboard frame lock portion 136 of the proximal inboard portion of the inboard frame understructure 120. In some embodiments, a distal end of the first proximal inboard mounting arm 123 and the second proximal inboard mounting arm 124 can be connected to a proximal end of the first transition understructure portion 126 and the second transition understructure portion 128, respectively. The first proximal inboard mounting arm 123 can have a reduced lateral width with respect to the first transition understructure portion 126 and the second proximal inboard mounting arm 124 can have a reduced lateral width with respect to the second transition understructure portion 128. In an example, the transition understructure portions 126, 128 and the proximal inboard mounting arms 123, 124 can be tapered at a tapered transition area between the two elements, as further depicted in FIG. 2C.

In some embodiments, a proximal end of the inboard frame lock portion 136 can be connected to a proximal tail portion that includes a first proximal tail 148 and a second proximal tail 150. The first proximal tail 148 can be connected to the first proximal inboard mounting arm 123 and the second proximal tail 150 can be connected to the second proximal inboard mounting arm 124. In an example, the proximal inboard mounting arms 123, 124 and the proximal tails 148, 150 can be tapered at a tapered tail transition area between the two elements, as further depicted in FIG. 2C.

The inboard frame lock portion 136 can include a first pair of inboard frame lock tabs 138-1, 138-2 and a second pair of inboard frame lock tabs 140-1, 140-2. In some embodiments, the inboard frame lock tabs 138-1, 138-2, 140-1, 140-2 can laterally extend outward from the first proximal inboard mounting arm 123 and the second proximal inboard mounting arm 124. In an example, the first pair of inboard frame lock tabs 138-1, 138-2 can laterally extend from the first proximal inboard mounting arm 123 away from tip longitudinal axis bb; and the second pair of inboard frame lock tabs 140-1, 140-2 can laterally extend from the second proximal inboard mounting arm 124 away from tip longitudinal axis bb.

FIG. 2C is an enlarged view of an inboard frame lock portion 136 of the inboard understructure 120 depicted in FIG. 2A, according to various embodiments of the present disclosure. As depicted with respect to a first inboard frame lock tab 140-1, each of the inboard frame lock tabs can include a distal tab edge 142-1 and a proximal tab edge 142-2. In some embodiments, the distal tab edge 142-1 and the proximal tab edge 142-2 can be perpendicular to the tip longitudinal axis bb, although not depicted. In some embodiments, the distal tab edge 142-1 and the proximal tab edge 142-2 can be formed at an angle $\theta'$ with respect to one another. The angle $\theta'$ can be in a range from 60 degrees to 10 degrees, in some embodiments. However, the angle $\theta'$ can be less than 10 degrees or greater than 60 degrees in some embodiments. As depicted, the angle $\theta'$ can be 30 degrees.

In some embodiments, a longitudinal length of each of the tabs can be approximately 0.036 inches, although the tabs can have a shorter or longer length. The tabs can be of a uniform longitudinal length in some embodiments and/or can be of different longitudinal lengths. In some embodiments, each of the tabs can have a lateral width of approximately 0.013 inches, although the lateral width of each tab can be greater or smaller. As depicted, the tabs can be longitudinally spaced apart. For example, with respect to the first inboard lock tab 140-1 and the second inboard lock tab 140-2, the longitudinal center of each tab can be longitudinally spaced apart by approximately 0.08 inches, although the tabs can be spaced closer or father apart with respect to one another.

As previously discussed in relation to FIG. 2B, the transition understructure portions 126, 128 and the proximal inboard mounting arms 123, 124 can include tapered transition areas 144, 146 between the transition understructure portions 126, 128 and the proximal inboard mounting arms 123, 124. The tapered transition areas 144, 146 can be tapered in a distal to proximal direction, away from the tip longitudinal axis bb. In some embodiments, the tapered transition areas 144, 146 can be formed at an angle $\theta''$ with respect to one another. The angle $\theta''$ can be in a range from 10 degrees to 180 degrees, in some embodiments. However, the angle $\theta''$ can be less than 10 degrees or greater than 180 degrees in some embodiments. In some embodiments, the angle $\theta''$ can be approximately 25 degrees.

As previously discussed in relation to FIG. 2B, the proximal inboard mounting arms 123, 124 and the proximal tails 148, 150 can include tapered tail transition areas 152, 154 between the proximal inboard mounting arms 123, 124 and the proximal tails 148, 150. The tapered tail transition areas 152, 154 can be tapered in a distal to proximal direction, away from the tip longitudinal axis bb. In some embodiments, the tapered tail transition areas 152, 154 can be formed an angle $\theta'''$ with respect to one another. The angle $\theta'''$ can be in a range from 10 degrees to 180 degrees, in some embodiments. However, the angle $\theta'''$ can be less than 10 degrees or greater than 180 degrees in some embodiments. In some embodiments, the angle $\theta'''$ can be approximately 25 degrees.

As previously discussed, each portion of the inboard frame understructure 120 (FIG. 2A, 2B), including the proximal tails 148, 150, proximal inboard mounting arms 123, 124, inboard arm understructures 121, 122, and flared head portion 130 can be formed from a planar substrate. For example, the planar substrate can have a rectangular cross-section, which can be beneficial, as further described herein. In some approaches, high density electrode mapping catheters can be assembled using tubular subassemblies for the inboard understructure and the outboard understructure. One reason for the use of tubing when assembling the understructures is to allow wire to be threaded through the tubing for connection of each individual microelectrode. This process can be labor and/or cost intensive, since each wire may be individually threaded through the tubing and individually connected with each microelectrode. Further, ensuring that a reliable electrical connection is established between each microelectrode and its wire can be challenging.

In addition, use of tubing can result in a less predictable deflection of the flexible tip portion since the walls of the tubing may be symmetrical and are not biased to bend in a particular manner. Embodiments of the present disclosure can provide for a more predictable deflection of the flexible tip portion 110. In addition, embodiments of the present disclosure can maintain a lateral spacing between electrodes disposed on the inboard understructure and an outboard understructure, as further discussed herein.

As depicted in FIGS. 2A and 2B, the inboard understructure 120 (and although not depicted, the outboard understructure) can be formed from a planar piece of material. In an example, the inboard understructure 120 (and the outboard understructure) can be formed from an understructure with a rectangular and/or square shaped cross-section. In some embodiments, the inboard understructure 120 and/or the outboard understructure can be a continuous element that is formed from a single unitary piece of material. As used herein, a rectangular cross-section can be defined as a cross-section having a greater width than thickness. However, in some embodiments, a rectangular cross-section can include a cross-section having a greater thickness than width. As used herein, a square cross-section can be defined as a cross-section having a same width and thickness.

Figure 2D:
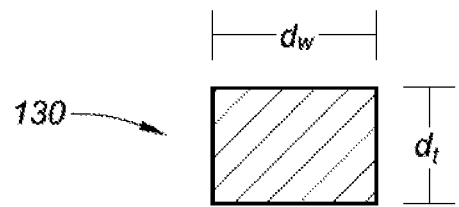
FIG. 2D is a cross-sectional view of a flared head portion of the inboard understructure depicted in FIG. 2B along line dd, according to various embodiments of the present disclosure.

FIG. 2D depicts a cross-section of a flared head portion 130 of the inboard understructure 120 depicted in FIG. 2B along line dd, according to various embodiments of the present disclosure. In some embodiments, the cross-section of the flared head portion 130 can be rectangular, as depicted in FIG. 2D, having a greater width than thickness. In some embodiments, the cross-section can be square, having a same width and thickness. In an example, a thickness at a longitudinal apex of the flared head portion 130 defined by line $d_t$ can be in a range from 0.0045 to 0.0065 inches. In some embodiments, the thickness at the longitudinal apex of the flared head portion 130 can be approximately 0.006 inches. In some embodiments, a longitudinal width (e.g., width extending along the longitudinal axis bb) at the longitudinal apex of the flared head portion 130 defined by line $d_w$ can be in a range from 0.007 to 0.009 inches. In some embodiments, the longitudinal width at the longitudinal apex of the flared head portion 130 can be approximately 0.008 inches.

Figure 2E:
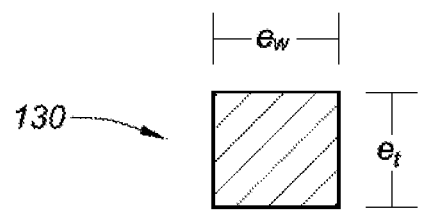
FIG. 2E is a cross-sectional view of a flared head portion of the inboard understructure depicted in FIG. 2B along line ee, according to various embodiments of the present disclosure.

FIG. 2E depicts a cross-section of a flared head portion 130 of the inboard understructure 120 depicted in FIG. 2B along line ee, according to various embodiments of the present disclosure. In some embodiments, the cross-section at a lateral apex of the flared distal head portion 130 can be square, as depicted in FIG. 2E, having a same width and thickness. In some embodiments, the cross-section at the lateral apex of the flared distal head portion 130 can be rectangular, having a greater width than thickness. In some embodiments, a thickness at the lateral apex of the flared head portion 130 defined by line $e_t$ can be in a range from 0.0045 to 0.0065 inches. In some embodiments, the thickness at the lateral apex of the flared head portion 130 can be approximately 0.006 inches. In some embodiments, a lateral width (e.g., width extending transverse to the longitudinal axis bb) at the lateral apex of the flared head portion 130 defined by line $e_w$ can be in a range from 0.005 to 0.007 inches. In some embodiments, the lateral width at the lateral apex of the flared head portion 130 can be approximately 0.006 inches.

Figure 2F:
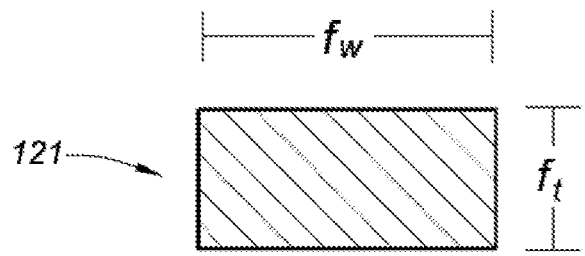
FIG. 2F is a cross-sectional view of a first inboard arm understructure of the inboard understructure depicted in FIG. 2B along line ff, according to various embodiments of the present disclosure.

FIG. 2F depicts a cross-section of a first inboard arm understructure 121 of the inboard understructure 120 depicted in FIG. 2B along line ff, according to various embodiments of the present disclosure. In some embodiments, the cross-section of the first inboard arm understructure 121 can be rectangular, as depicted in FIG. 2F, having a greater width than thickness. In some embodiments, the cross-section can be square, having a same width and thickness. In some embodiments, a thickness at the first inboard arm understructure 121 defined by line $f_t$ can be in a range from 0.0045 to 0.0065 inches. In some embodiments, the thickness at the first inboard arm understructure 121 can be approximately 0.006 inches. In some embodiments, a lateral width at the first inboard arm understructure 121 defined by line $f_w$ can be in a range from 0.0125 to 0.0135 inches. In some embodiments, the lateral width at the lateral apex of the flared head portion 130 can be approximately 0.013 inches. The second inboard arm understructure 122 can be of the same dimensions as the first inboard arm understructure 121. Accordingly, in some embodiments, the inboard understructure 120 can have a uniform thickness and a varying width.

FIG. 3A is a top view of an outboard understructure 170 (also referred to herein as outer understructure) of a high density electrode mapping catheter in FIG. 1A, according to various embodiments of the present disclosure. In some embodiments, the outboard understructure 170 can be formed from a flexible or spring-like material such as Nitinol and/or a flexible substrate, as previously discussed with respect to the inboard understructure. The outboard understructure 170 can include a first outboard arm understructure 172 and a second outboard arm understructure 174. As depicted, the outboard understructure 170 can include a first proximal inboard mounting arm 176 and a second proximal inboard mounting arm 178. The proximal inboard mounting arms 176, 178 can be inserted into a distal end of the catheter 107 (FIG. 1A, 1B) and can be used to connect the flexible tip portion 110 (FIG. 1A, 1B) to the distal end of the catheter 107. In some embodiments, the proximal outboard mounting arms 176, 178 can be inserted through a torsional spacer, as discussed herein.

In some embodiments, the outboard understructure 170 can define a tip longitudinal axis, depicted by line b'b'. In some embodiments, the outboard understructure 170 can be formed from a continuous element that includes a first rectangular cross-section. For example, the outboard understructure 170 can include the first proximal outboard mounting arm 176 and second proximal outboard mounting arm 178, which can extend along the tip longitudinal axis. The outboard understructure 170 can include a first outboard arm understructure 172 that extends distally from the first proximal inboard mounting arm 176 and can include a second outboard arm understructure 174 that extends distally from the second proximal outboard mounting arm 178. In some embodiments, the first outboard arm understructure 172 and the second outboard arm understructure 174 can extend parallel to the tip longitudinal axis b'b' and to one another.

In some embodiments, a first outboard transition understructure portion 180 can be disposed between the first proximal outboard mounting arm 176 and the first outboard arm understructure 172. The first outboard transition understructure portion 180 can be laterally flared away from the tip longitudinal axis b'b'. Additionally, a second outboard transition understructure portion 181 can be disposed between the second proximal outboard mounting arm 178 and the second outboard arm understructure 174. The second outboard transition understructure portion 181 can be laterally flared away from the tip longitudinal axis b'b'. In an example, the first outboard transition understructure portion 180 and the second outboard transition understructure portion 181 can be flared away from one another.

In some embodiments, the outboard understructure 170 includes a head portion 182 that is connected to distal ends of the first and second outboard arm understructures 172, 174. In some embodiments, the head portion 182 can be formed from a first tapered element 184 and a second tapered element 186 that each extend distally toward the tip longitudinal axis b'b' and converge at the longitudinal axis b'b'. In an example, the outboard understructure 170 can be symmetrical along either side of the tip longitudinal axis b'b'.

In some embodiments, the proximal outboard portion of the inboard frame understructure 170 can include the first proximal outboard mounting arm 176 and the second proximal outboard mounting arm 178. In an example, the proximal outboard portion of the outboard frame understructure 170 can include an outboard frame lock portion 188, which is further discussed in relation to FIG. 3B.

In some embodiments, a distal end of the first proximal outboard mounting arm 176 and the second proximal outboard mounting arm 178 can be connected to a proximal end of the first outboard transition understructure portion 180 and the second outboard transition understructure portion 181, respectively. The first proximal outboard mounting arm 176 can have a reduced lateral width with respect to the first outboard transition understructure portion 180 and the second proximal outboard mounting arm 178 can have a reduced lateral width with respect to the second outboard transition understructure portion 181. In an example, the outboard transition understructure portions 180, 181 and the proximal outboard mounting arms 176, 178 can be tapered at an outboard tapered transition area between the two elements, as further depicted in FIG. 3B.

In some embodiments, a proximal end of the outboard frame lock portion 188 can be connected to a proximal outboard tail portion that includes a first proximal outboard tail 189 and a second proximal outboard tail 190. The first proximal outboard tail 189 can be connected to the first proximal outboard mounting arm 176 and the second proximal outboard tail 190 can be connected to the second proximal outboard mounting arm 178. In an example, the proximal outboard mounting arms 176, 178 and the proximal outboard tails 189, 190 can be tapered at a tapered outboard tail transition area between the two elements, as further depicted in FIG. 3B.

The outboard frame lock portion 188 can include a first pair of outboard frame lock tabs 192-1, 192-2 and a second pair of outboard frame lock tabs 194-1, 194-2. In some embodiments, the outboard frame lock tabs 192-1, 192-2, 194-1, 194-2 can laterally extend inward from the first proximal outboard mounting arm 176 and the second proximal inboard mounting arm 178. In an example, the first pair of outboard frame lock tabs 192-1, 192-2 can laterally extend from the first proximal inboard mounting arm 176 toward the tip longitudinal axis b'b; and the second pair of outboard frame lock tabs 194-1, 194-2 can laterally extend from the second proximal inboard mounting arm 178 toward the tip longitudinal axis b'b'.

FIG. 3B is an enlarged view of an outboard frame lock portion 188 of the outboard understructure 170 depicted in FIG. 3A, according to various embodiments of the present disclosure. As depicted with respect to a first outboard frame lock tab 194-1, each of the outboard frame lock tabs can include a distal tab edge 200-1 and a proximal tab edge 200-2. In some embodiments, the distal tab edge 200-1 and the proximal tab edge 200-2 can be perpendicular to the tip longitudinal axis b'b', although not depicted. In some embodiments, the distal tab edge 200-1 and the proximal tab edge 200-2 can be formed at an angle $\theta^A$ with respect to one another. The angle $\theta^A$ can be in a range from 60 degrees to 10 degrees, in some embodiments. However, the angle θ' can be less than 10 degrees or greater than 60 degrees in some embodiments. As depicted, the angle θ' can be 30 degrees. In some embodiments, the angle $\theta^A$ can be the same as the angle θ', to ensure that inboard frame lock portion 136 fits together with the outboard frame lock portion 188.

In some embodiments, a first pair of lock grooves 196-1, 196-2 and a second pair of lock grooves 198-1, 198-2 can be formed in the outboard frame lock portion 188. In an example, the lock grooves can be formed on the inside (e.g., side towards the tip longitudinal axis b'b') of each first and second proximal outboard mounting arms 178. In an example, the first and second pairs of inboard frame lock tabs 138-1, 138-2, 140-1, 140-2 (FIG. 2B, 2C) can be inserted into respective ones of the lock grooves 196-1, 196-2, 198-1, 198-2, as further discussed herein.

In some embodiments, the transition understructure portions 180, 181 and the proximal outboard mounting arms 176, 187 can include tapered transition areas 202, 204 between the transition understructure portions 180, 181 and the proximal inboard mounting arms 176, 178. The tapered transition areas 202, 204 can be tapered in a distal to proximal direction, toward the tip longitudinal axis b'b'. In some embodiments, the tapered transition areas 202, 204 can be formed at an angle $\theta^B$ with respect to one another. The angle $\theta^B$ can be in a range from 10 degrees to 180 degrees, in some embodiments. However, the angle $\theta^B$ can be less than 10 degrees or greater than 180 degrees in some embodiments. In some embodiments, the angle $\theta^B$ can be approximately 25 degrees.

As previously discussed in relation to FIG. 3A, the proximal outboard mounting arms 176, 178 and the proximal outboard tails 189, 190 can include tapered tail transition areas 206, 208 between the proximal outboard mounting arms 176, 178 and the proximal outboard tails 189, 190. The tapered tail transition areas 206, 208 can be tapered in a distal to proximal direction, toward the tip longitudinal axis b'b'. In some embodiments, the tapered tail transition areas 206, 208 can be formed at an angle $\theta^C$ with respect to one another. The angle $\theta^C$ can be in a range from 10 degrees to 180 degrees, in some embodiments. However, the angle $\theta^C$ can be less than 10 degrees or greater than 180 degrees in some embodiments. In some embodiments, the angle $\theta^C$ can be approximately 46 degrees.

As previously discussed, each portion of the outboard frame understructure 170, including the proximal tails 189, 190, proximal outboard mounting arms 176, 178, outboard arm understructures 172, 174, and head portion 182 can be formed from a planar substrate. For example, the planar substrate can have a rectangular cross-section, which can be beneficial, as further described herein. As previously discussed, in some approaches, high density electrode mapping catheters can be assembled using tubular subassemblies for the inboard understructure and the outboard understructure. However, use of tubing can result in a less predictable deflection of the flexible tip portion since the walls of the tubing may be symmetrical and are not biased to bend in a particular manner. Embodiments of the present disclosure can provide for a more predictable deflection of the flexible tip portion 110 and the inboard understructure 120 (FIGS. 2A, 2B) and the outboard understructure 170.

As depicted in FIGS. 3A and 3B, the outboard understructure 170 can be formed from a planar piece of material. In an example, the outboard understructure 170 can be formed from an understructure with a rectangular and/or square shaped cross-section. In some embodiments, the outboard understructure 170 can be a continuous element that is formed from a single unitary piece of material.

Figure 3C:
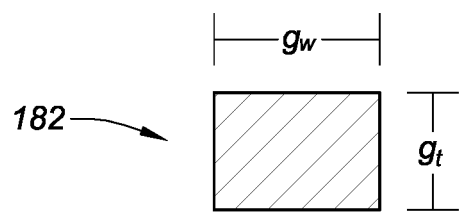
FIG. 3C is a cross-sectional view of a head portion of the outboard understructure depicted in FIG. 3B along line gg, according to various embodiments of the present disclosure.

FIG. 3C depicts a cross-section of a head portion 182 of the outboard understructure 170 depicted in FIG. 3B along line gg, according to various embodiments of the present disclosure. In some embodiments, a thickness at a longitudinal apex of the head portion 182 defined by line $g_t$ can be in a range from 0.0045 to 0.0065 inches. In some embodiments, the thickness at the longitudinal apex of the flared head portion 130 can be approximately 0.006 inches. In some embodiments, a longitudinal width (e.g., width extending along the longitudinal axis b'b') at the longitudinal apex of the head portion 182 defined by line g, can be in a range from 0.0075 to 0.0085 inches. In some embodiments, the longitudinal width at the longitudinal apex of the flared head portion 130 can be approximately 0.008 inches.

Figure 3D:
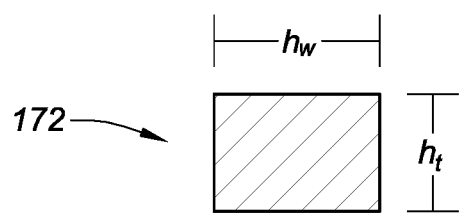
FIG. 3D is a cross-sectional view of the first outboard arm understructure of the outboard understructure depicted in FIG. 3A along line hh, according to various embodiments of the present disclosure.

FIG. 3D depicts a cross-section of the first outboard arm understructure 172 of the outboard understructure 170 depicted in FIG. 3A along line hh, according to various embodiments of the present disclosure. In some embodiments, a thickness at the first outboard arm understructure 172 defined by line $h_t$ can be in a range from 0.0045 to 0.0065 inches. In some embodiments, the thickness at the first outboard arm understructure 172 can be approximately 0.006 inches. In some embodiments, a lateral width (e.g., width extending transverse to the longitudinal axis b'b') at the first outboard arm understructure 172 defined by line $h_w$ can be in a range from 0.0125 to 0.0135 inches. In some embodiments, the lateral width at the first outboard arm understructure 172 can be approximately 0.013 inches. The second outboard arm understructure 174 can have a similar construction as discussed in relation to the first outboard arm understructure 172.

Figure 4:
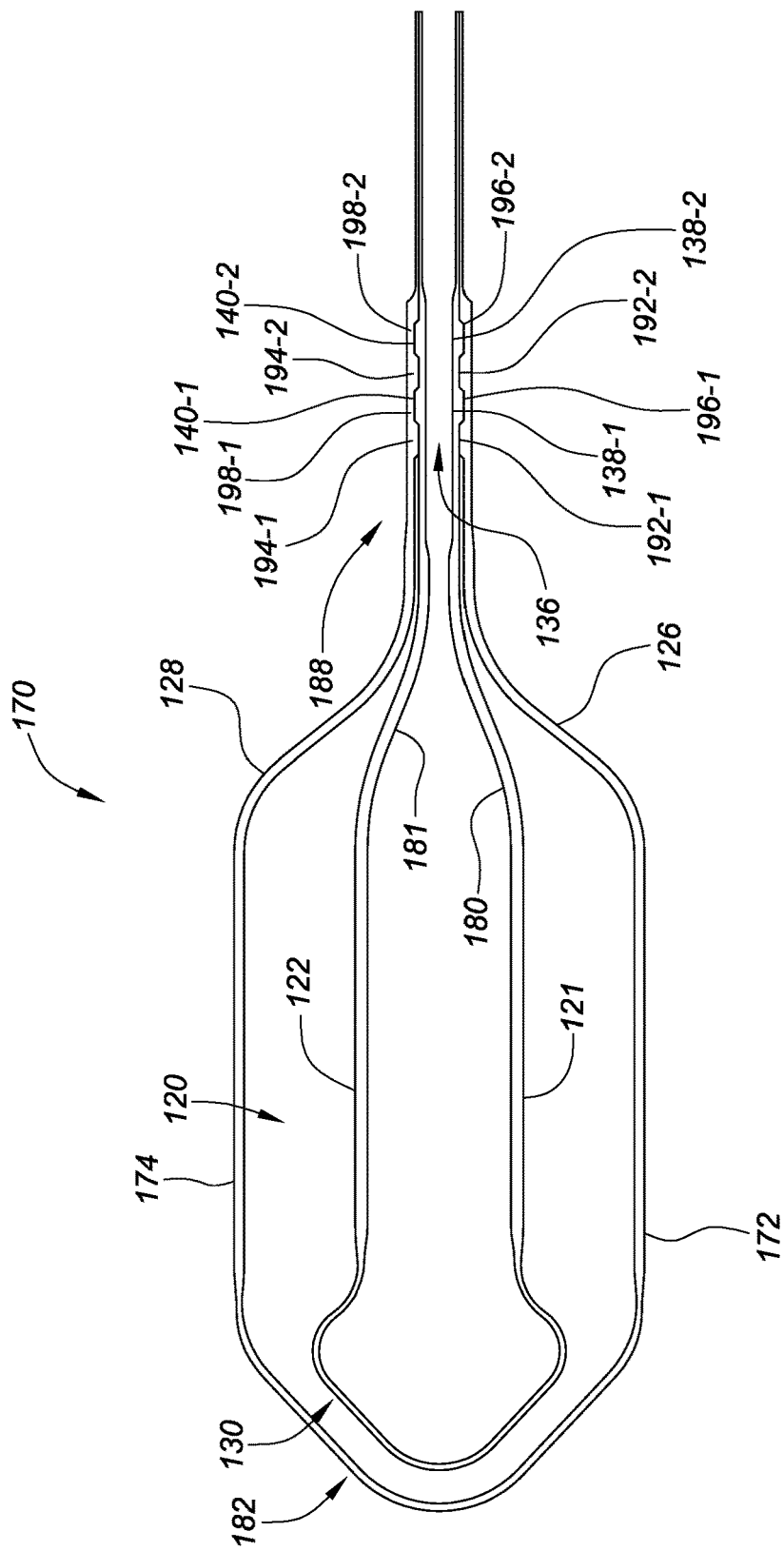
FIG. 4 depicts the inboard understructure in FIG. 2A and the outboard understructure in FIG. 3A with interlocking inboard frame lock portion and outboard frame lock portion, according to various embodiments of the present disclosure.

FIG. 4 depicts the inboard understructure 120 depicted in FIG. 2A and the outboard understructure 170 depicted in FIG. 3A with interlocking inboard frame lock portion 136 and outboard frame lock portion 188, according to various embodiments of the present disclosure. The inboard understructure 120 and the outboard understructure 170 include those features previously discussed in relation to FIGS. 2A to 3D. As depicted, the inboard frame lock portion 136 is depicted as interlocking with the outboard frame lock portion 188. In an example, the inboard frame lock tabs 138-1, 138-2, 140-1, 140-2 are disposed in the lock grooves 196-1, 196-2, 198-1, 198-2 and adjacent to the outboard frame lock tabs 192-1, 192-2, 194-1, 194-2. This can create an interlocking fit between the inboard frame lock portion 136 and the outboard frame lock portion 188. The interlocking fit can prevent longitudinal movement of the inboard understructure 120 with respect to the outboard understructure 170, in some embodiments. Although four inboard frame lock tabs 138-1, 138-2, 140-1, 140-2 and four outboard frame lock tabs 192-1, 192-2, 194-1, 194-2 are depicted, greater than or fewer than four inboard and/or outboard frame lock tabs can be included on the inboard and outboard understructures. In some embodiments, the inboard frame lock portion 136 can be disposed in the outboard frame lock portion 188 such that a top surface of the inboard frame lock portion 136 is flush with a top surface of the outboard frame lock portion 188; and a bottom surface of the inboard frame lock portion 136 is flush with a bottom surface of the outboard frame lock portion 188.

In some embodiments, the first and second outboard transition understructure portions 126, 128 can be formed at descending angles in a distal to proximal direction and the understructure forming the head portion 182 and flared head portion 130 can be formed at ascending angles in a distal to proximal direction. This can increase an ease of delivery and withdrawal through a sheath and also during manufacturing of the electrodes that are disposed on the inboard understructure 120 and/or the outboard understructure 170. For example, during assembly, electrodes can be slid over the understructure in a proximal to distal direction. The angle of the outboard transition understructure can allow for easier sliding of the electrodes over the understructure.

Figure 5A:
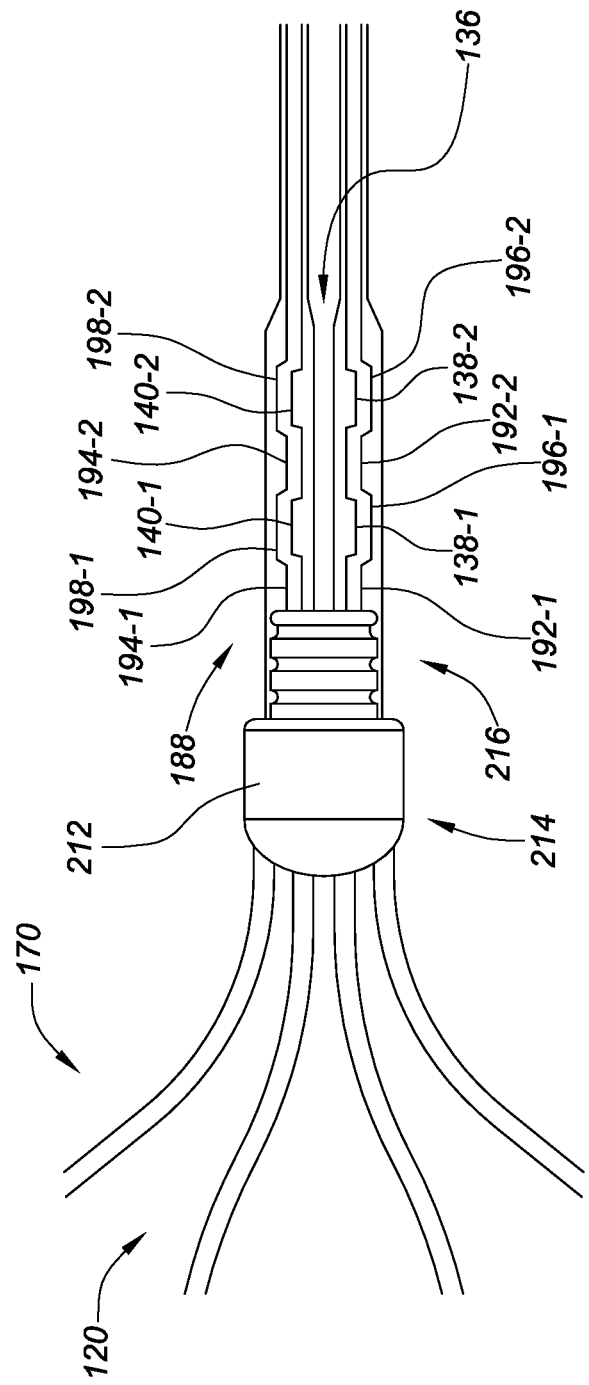
FIG. 5A depicts the inboard understructure in FIG. 2A and the outboard understructure depicted in FIG. 3A with interlocking inboard frame lock portion and outboard frame lock portion and a connector, according to various embodiments of the present disclosure.

FIG. 5A depicts the inboard understructure 120 depicted in FIG. 2A and the outboard understructure 170 depicted in FIG. 3A with interlocking inboard frame lock portion 136 and outboard frame lock portion 188 and a connector 212, according to various embodiments of the present disclosure. A gap is depicted between the inboard frame lock portion 136 and the outboard frame lock portion 188. In some embodiments, a connector 212 can be disposed at a distal end of the inboard frame lock portion 136 and outboard frame lock portion 188, as depicted. The inboard understructure 120 and the outboard understructure 170 can longitudinally extend through the connector 212.

In an example, the connector 212 can include a connector head portion 214 and a mount portion 216 and can be formed from a polymer or metal. In some embodiments, the mount portion 216 can be cylindrical in shape and can be sized to be inserted into a distal end of a catheter shaft. In some embodiments, an adhesive can be applied between the catheter shaft and the mount portion 216 and/or a mechanical connector can be used to secure the catheter shaft to the mount portion 216. In some embodiments, a series of circumferential grooves can extend around a circumference of the mount portion 216. The circumferential grooves can provide an area for an adhesive to collect when connecting the connector 212 to the catheter shaft. In some embodiments, the connector head portion 214 can have an outer diameter that is greater than the mount portion 216 and can be equal to an outer diameter of a catheter shaft. A distal end of the head portion 214 can be dome shaped, as depicted, to form an atraumatic tip.

Figure 5B:
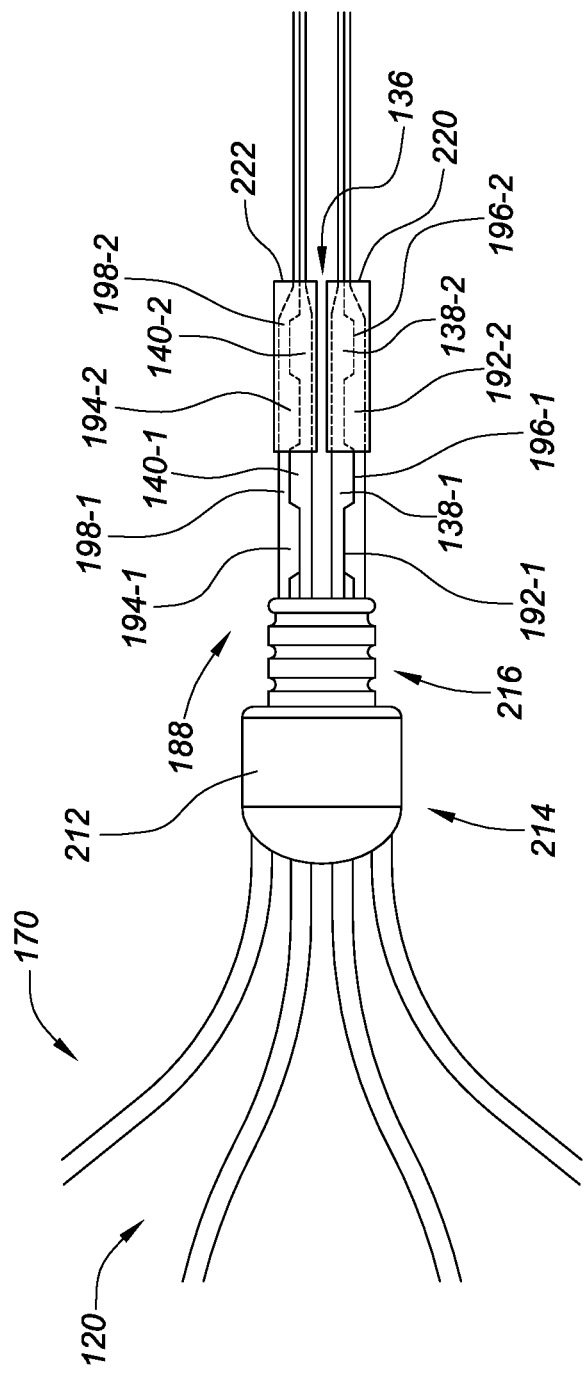
FIG. 5B depicts the inboard understructure and outboard understructure in FIG. 5A with tubing disposed around the interlocking inboard frame lock portion and outboard frame lock portion, according to various embodiments of the present disclosure.

FIG. 5B depicts the inboard understructure 120 and outboard understructure 170 depicted in FIG. 5A with tubing 220, 222 disposed around the interlocking inboard frame lock portion 136 and outboard frame lock portion 188, according to various embodiments of the present disclosure. In some embodiments, a first section of tubing 220 and a second section of tubing 222 can each be disposed around the interlocking portions of the inboard frame lock portion 136 and outboard frame lock portion 188. The interlocking portions of the inboard frame lock portion 136 and the outboard frame lock portion 188 disposed within the first and second section of tubing 220, 222 is depicted in phantom. In an example, the first section of tubing 220 and the second section of tubing 222 can include an inner diameter that is the same or larger than a lateral width of the interlocking portions of the inboard frame lock portion 136 and the outboard frame lock portion 188. The first section of tubing 220 and the second section of tubing 222 can be slid longitudinally over a proximal portion of the interlocking portions of the inboard frame lock portion 136 and the outboard frame lock portion 188, such that the interlocking portions of the inboard frame lock portion 136 and the outboard frame lock portion 188 are disposed in respective lumens of the first and second sections of tubing 220, 222.

Although the first and second sections of tubing 220, 222 are depicted as extending over the proximal portion of the interlocking portions of the inboard frame lock portion 136 and the outboard frame lock portion 188, the first and second section of tubing 220, 222 can extend more distally. For example, the first and second section of tubing 220, 222 can extend to the proximal end of the coupler 212. In some embodiments, the lumens of the first and second sections of tubing 220, 222 can be filled with an adhesive to secure the interlocking portions of the inboard frame lock portion 136 and the outboard frame lock portion 188. In some embodiments, the first and second sections of tubing 220, 222 can be heat shrink tubing, which can be heated and shrunk to secure the interlocking portions of the inboard frame lock portion 136 and the outboard frame lock portion 188.

Figure 6:
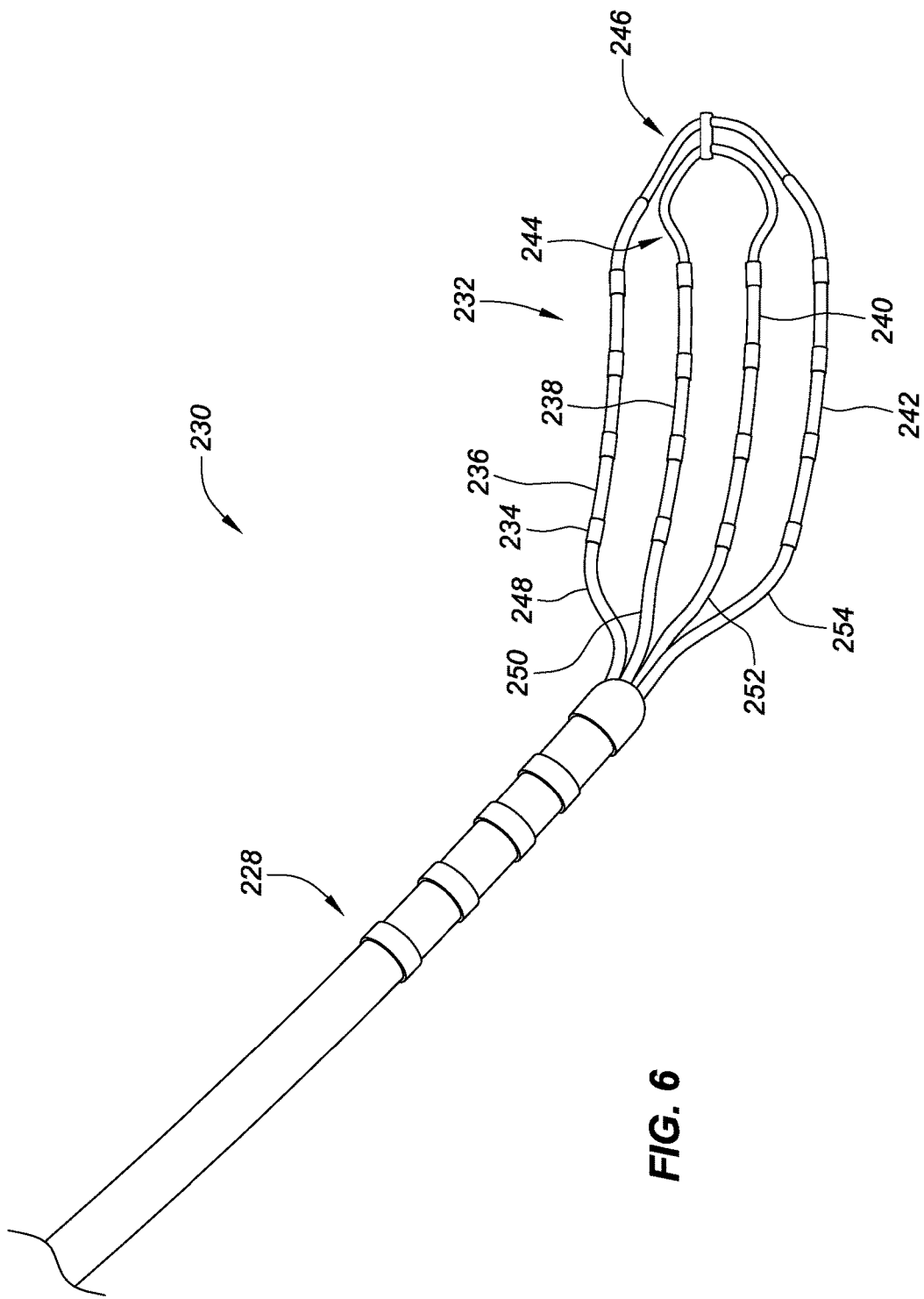
FIG. 6 depicts an isometric side and top view of a high density electrode mapping catheter being deflected, according to various embodiments of the present disclosure.

FIG. 6 depicts an isometric side and top view of a high density electrode mapping catheter 230 being deflected, according to various embodiments of the present disclosure. In some embodiments, the high density electrode mapping catheter includes a flexible tip portion 232 that forms a flexible array of microelectrodes 334, which is disposed at a distal end of a catheter shaft 228. This planar array (or 'paddle' configuration) of microelectrodes 234 comprises four side-by-side, longitudinally-extending arms 236, 238, 240, 242, which can form a flexible framework on which the microelectrodes 234 are disposed. The four microelectrode-carrier arms comprise a first outboard arm 236, a second outboard arm 242, a first inboard arm 238, and a second inboard arm 240. These arms can be laterally separated from each other. The inboard portion of the flexible tip 232 can include a flared head portion 244 and the outboard portion of the flexible tip 232 can include a head portion 246. The first outboard arm 236 and the second outboard arm 242 can include an outboard understructure and the first inboard arm 238 and the second inboard arm 240 can include an inboard understructure, as previously discussed. The first and second inboard arms 238, 240, as well as the flared head portion 244, can include a first and second inboard arm understructure that is formed from an element that includes a rectangular cross-section and the first and second outboard arms 236, 242, as well as the head portion 246, can include a first and second outboard arm understructure that is formed from an element that includes a rectangular cross-section, as previously discussed herein. In some embodiments, the flexible tip portion 232 can include a first outboard transition portion 248 and a second outboard transition portion 254. In some embodiments, the flexible tip portion 232 can include a first inboard transition portion 250 and a second inboard transition portion 252.

in some embodiments, as previously discussed and depicted in relation to FIGS. 2A to 3D, the understructure that forms the flared head portion 244 can have a reduced cross-sectional width in relation to the understructure that forms the inboard arms 238, 240. In addition, the understructure that forms the head portion 246 can have a reduced cross-sectional width in relation to the understructure that forms the outboard arms 236, 242. This reduced cross-sectional width of the understructure forming the flared head portion 244 and the head portion 246 can increase a resiliency of the head portions 244, 246 and cause the head portions 244, 246 to be less traumatic to cardiac tissue. For example, because of the reduced cross-sectional width, the head portions can have an increased flexibility and a reduced amount of force can be required to deflect the head portions 244, 246, providing for an atraumatic design.

In some embodiments, as previously discussed and depicted in relation to FIGS. 2A to 3D, the first outboard arm 236, second outboard arm 242, first outboard transition portion 248, and second outboard transition portion 254 can be formed from an understructure that has an increased cross-sectional width in relation to the understructure that forms the head portion 246. In addition, the first inboard arm 238, second inboard arm 240, first inboard transition portion 250, and second inboard transition portion 252 can be formed from an understructure that has an increased cross-sectional width in relation to the understructure that forms the flared head portion 244. In some embodiments, the increased cross-sectional width of the understructure that forms the inboard and outboard arms, as well as the inboard and outboard transition portions can provide for a more gradual bend of the flexible tip portion 232 located proximal to the flared head portion 244 and the head portion 246, The more gradual bend can be beneficial in making homogeneous (e.g. uniform) cardiac tissue contact with all of the electrodes disposed on the inboard and outboard arms and/or the inboard and outboard transition portions.

In addition, because the understructure that forms each component of the flexible tip portion 232 includes a rectangular cross-section, the lateral spacing between each one of the microelectrodes disposed on the flexible tip portion 232 can be maintained when various lateral forces (e.g., pinch) are applied to the flexible tip portion, which can be encountered in relation to various anatomical conditions. For example, with further mference to FIG. 1, an electrode spacing can be maintained even when a lateral force is applied to the flexible tip portion 110 in the direction of arrows 112-1, 112-2. In some approaches where an understructure that forms the inboard and outboard arms is made from a tubular material, when a lateral force is applied to the inboard and/or outboard arms, the arms can bend inward toward the longitudinal axis aa. For example, if the outboard arms 103, 106 included a tubular understructure, the outboard arms 103, 106 would be pushed laterally inward toward the longitudinal axis and towards the inboard arms 104, 105 in response to a force being applied in the direction of arrows 112-1, 112-2. This can reduce a spacing between the microelectrodes disposed on the outboard arms and the microelectrodes disposed on the inboard arms, thus causing interference between the microelectrodes. However, embodiments of the present disclosure can maintain the spacing between the inboard arms and the outboard arms, as well as the microelectrodes disposed on the inboard arms and the outboard arms, In an example, as discussed herein, the understructure that forms the inboard arms 104, 105 and the outboard arms 103, 106 can have a rectangular cross-section, as discussed in relation to FIGS. 2A to 3D. For instance, the understructure that forms the inboard arms 104, 105 and the outboard arms 103, 106 can have an increased lateral width versus a lateral width of the understructure that forms the head portions. Additionally, a dimension of the lateral width can be greater than a dimension of the thickness of the understructure that forms the inboard arms 104, 105 and the outboard arms 103, 106. This can prevent the outboard arms 103, 106 from deflecting inward toward the longitudinal axis aa, thus maintaining a lateral spacing between the microelectrodes 102. For example, a lateral spacing can be maintained between a first microelectrode 102-1 disposed on the first outboard arm 103 and a third microelectrode 102-3 disposed on the first inboard arm 104 in the presence of a lateral force in the direction of arrows 112-1, 112-2. Likewise, a lateral spacing can be maintained between a second microelectrode 102-2 disposed on the first outboard arm 103 and a fourth microelectrode 102-4 disposed on the first inboard arm 104 in the presence of a lateral force in the direction of arrows 112-1, 112-2.

Instead of deflecting laterally, the inboard understructure and/or the outboard understructure can deflect upward or downward, thus avoiding electrode to electrode contact, as further discussed in relation to FIGS. 7A to 7D. FIG. 7A depicts a front view of a high density electrode mapping catheter 260 in a first deflection state 262-1 and a second deflection state 262-2, according to various embodiments of the present disclosure. The high density electrode mapping catheter 260 includes an outboard portion 264 formed from an outboard understructure. The outboard understructure can be formed from an element with a rectangular cross-section, as discussed herein. The high density electrode mapping catheter 260 can include a connector 266 disposed on the distal end of a catheter shaft 282 (depicted in FIGS. 7B and 7D), as well as a distal coupler 268 that couples an inboard portion 280 (depicted in FIGS. 7B and 7D) with the outboard portion 264. As depicted, when an amount of lateral force applied to the outboard portion 264 is zero, the understructure of the outboard portion 264 can be in a first deflection state 262-1 (e.g., a natural deflection state), extending laterally with respect to a longitudinal axis of the high density electrode mapping catheter 260. However, when a lateral force is applied to the outboard portion 264 in the direction of arrows 270-1, 270-2, the outboard portion can deflect upward into a second deflection state 262-2, depicted in phantom. Thus, the outboard portion 264 can deflect upward into the second deflection state 262-2, rather than deflecting laterally inward toward a longitudinal axis of the high density electrode mapping catheter 260.

FIG. 7B depicts an isometric, side, front, and top view of the high density electrode mapping catheter 260 in the second deflection state 262-2 in FIG. 7A, according to various embodiments of the present disclosure. The high density electrode mapping catheter 260 includes those features discussed in relation to FIG. 7A, for example, the high density electrode mapping catheter 260 includes the outboard portion 264, the inboard portion 280, distal coupler 268, connector 266 and catheter shaft 282. As depicted, the outboard portion 264 and the inboard portion 280 can be deflected upward in response to a lateral force being subjected to the high density mapping catheter 260 (e.g., the outboard portion 264 and/or inboard portion 280). In an example, because the understructure that forms a first outboard arm 282 and second outboard arm 288 and the understructure that forms a first inboard arm 284 and second inboard arm 286 of the high density electrode mapping catheter 260 have a rectangular cross-section (e.g., have an increased lateral width versus thickness), the first and second outboard arms 282, 288 can deflect upward instead of deflecting laterally inward toward a longitudinal axis of the high density electrode mapping catheter 260.

FIG. 7C depicts a front view of the high density electrode mapping catheter 260 depicted in FIGS. 7A and 7B in the first deflection state 262-1 and a third deflection state 262-3, according to various embodiments of the present disclosure. The high density electrode mapping catheter 260 includes the outboard portion 264 formed from an outboard understructure, connector 266 disposed on the distal end of the catheter shaft 282 (depicted in FIGS. 7B and 7D), as well as the distal coupler 268 that couples an inboard portion 280 (depicted in FIGS. 7B and 7D) with the outboard portion 264. As depicted, when an amount of lateral force applied to the outboard portion 264 is zero, the understructure of the outboard portion 264 can be in a first deflection state 262-1 (e.g., a natural deflection state), extending laterally with respect to a longitudinal axis of the high density electrode mapping catheter 260. However, when a lateral force is applied to the outboard portion 264 in the direction of arrows 270-1', 270-2', the outboard portion 264 can deflect downward into a third deflection state 262-3, depicted in phantom. Thus, the outboard portion 264 can deflect downward into the third deflection state 262-3, rather than deflecting laterally inward toward a longitudinal axis of the high density electrode mapping catheter 260. In some embodiments, a deciding factor associated with whether the outboard portion 264 or inboard portion 280 of the high density electrode mapping catheter 260 will deflect downward or upward can be associated with an angle at which the lateral force is applied to the outboard portion 264 and/or inboard portion 280.

FIG. 7D depicts an isometric, side, front, and top view of the high density electrode mapping catheter 260 in the third deflection state 262-3 in FIG. 7C, according to various embodiments of the present disclosure. The high density electrode mapping catheter 260 includes those features discussed in relation to FIG. 7C, for example, the high density electrode mapping catheter 260 includes the outboard portion 264, the inboard portion 280, distal coupler 268, connector 266 and catheter shaft 282. As depicted, the outboard portion 264 and the inboard portion 280 can be deflected downward in response to a lateral force being subjected to the high density mapping catheter 260 (e.g., the outboard portion 264 and/or inboard portion 280). In an example, because the understructure that forms the first outboard arm 282 and second outboard arm 288 and the understructure that forms the first inboard arm 284 and second inboard arm 286 of the high density electrode mapping catheter 260 have a rectangular cross-section (e.g., have an increased lateral width versus thickness), the first and second outboard arms 282, 288 can deflect downward instead of deflecting laterally inward toward a longitudinal axis of the high density electrode mapping catheter 260. This can maintain a spacing between microelectrodes disposed on the inboard and outboard arms.

Figure 8:
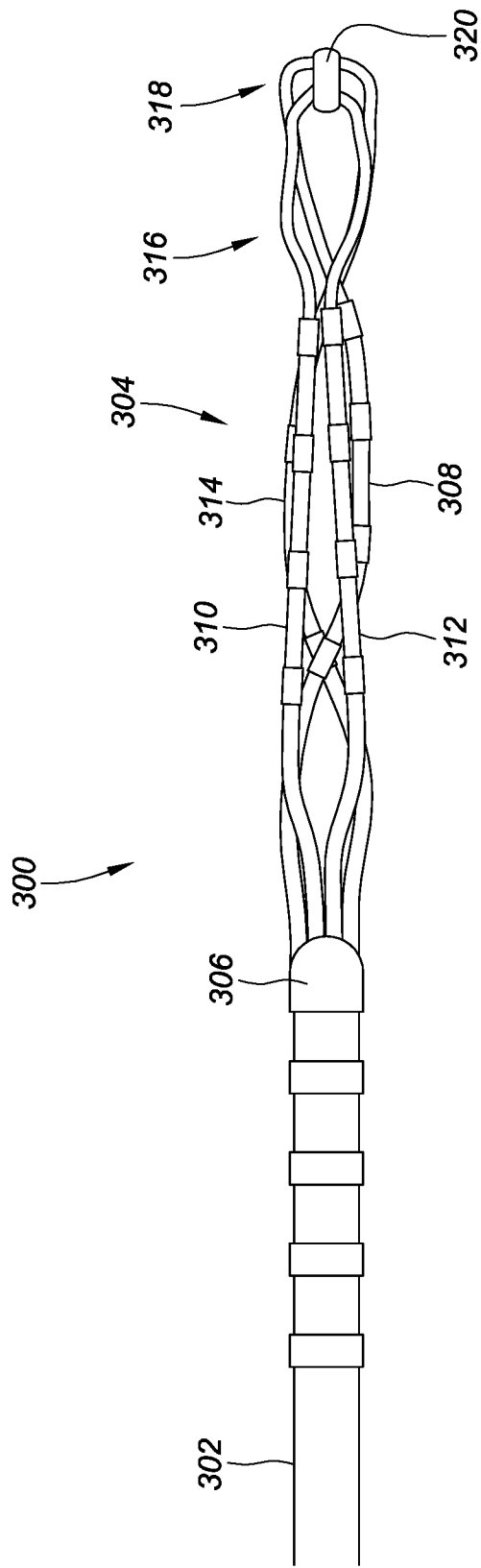
FIG. 8 depicts a top view of a high density electrode mapping catheter with a flexible tip portion in a collapsed state, according to various embodiments of the present disclosure.

FIG. 8 depicts a top view of a high density electrode mapping catheter 300 with a flexible tip portion 304 in a collapsed state, according to various embodiments of the present disclosure. In some embodiments, the high density electrode mapping catheter 300 can include a catheter shaft 302. The catheter shaft 302 can include a proximal end and a distal end. The distal end can include a connector 306, which can couple the distal end of the catheter shaft 302 to a proximal end of the flexible tip portion 304 (e.g., planar array). The flexible tip portion 304 can include an outboard portion that includes a first outboard arm 308, second outboard arm 214, and head portion 318 and can include an inboard portion that includes a first inboard arm 310 and second inboard arm 312 and a flared head portion 316. The head portion 318 and the flared head portion 316 can be connected at their respective distal ends via a distal coupler 320, in some embodiments.

As depicted, the flexible tip portion 304 is in a stored state. The flexible tip portion 304 can be in such a state when it is stored in a sheath for introduction into a body, in an example. Upon introduction of the flexible tip portion 304 into the sheath, the outboard portion and inboard portion of the flexible tip portion 304 can be laterally compressed toward a longitudinal axis of the high density electrode mapping catheter 300. For example, the outboard portion and inboard portion of the flexible tip portion 304 can be laterally compressed by the inner walls of the sheath. In some embodiments, the flared head portion 316 of the inboard portion can be straightened as the inboard portion and the outboard portion are laterally compressed toward the longitudinal axis of the flexible tip portion 304. In some approaches that do not have a flared head portion 316, as the inboard portion and the outboard portion are laterally compressed, a hook can be formed in the distal end of the flexible tip portion 304. Embodiments of the present disclosure can include for the flared head portion 316, which can provide for a slack portion, which can be lengthened when the inboard portion and the outboard portion are laterally compressed. For example, the flared distal head (e.g., spade shaped portion) can compensate for the extra length needed to match the outer frame total length when folded during delivery and/or withdrawal through the sheath, which can prevent the hook from forming.

Embodiments are described herein of various apparatuses, systems, and/or methods. Additional aspects of the present disclosure will be made apparent upon review of the material in Appendix A, attached herewith. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it may be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for a high density electrode mapping catheter has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A flexible catheter tip, comprising:
   an inboard understructure that defines a tip longitudinal axis, wherein the inboard understructure is formed from a first continuous element that includes a first rectangular cross-section; and
   an outboard understructure that extends along the tip longitudinal axis, wherein the outboard understructure is formed from a second continuous element that includes a second rectangular cross-section, wherein:
      the inboard understructure includes a first proximal inboard mounting arm and second proximal inboard mounting arm that extend generally parallel to the tip longitudinal axis;
      the outboard understructure includes a first proximal outboard mounting arm and a second proximal outboard mounting arm that extend generally parallel to the tip longitudinal axis;
      opposing faces of the first proximal inboard mounting arm and the first proximal outboard mounting arm include a first set of frame locks; and
      opposing faces of the second proximal inboard mounting arm and the second proximal outboard mounting arm include a second set of frame locks corresponding to the first set of frame locks, wherein the first set of frame locks and the second set of frame locks are configured to interlock with one another.

2. The flexible catheter tip of claim 1, wherein the inboard understructure includes:
   a first inboard arm understructure that extends distally from the first proximal inboard mounting arm; and
   a second inboard arm understructure that extends distally from the second proximal inboard mounting arm.

3. The flexible catheter tip of claim 2, wherein the inboard understructure includes a flared head portion connected to distal ends of the first and second inboard understructure.

4. The flexible catheter tip of claim 1, wherein the first set of frame locks include a plurality of interlocking tabs that extend from the opposing faces of the first proximal inboard mounting arm and the first proximal outboard mounting arm and the second set of frame locks include a plurality of interlocking tabs that extend from the opposing faces of the second proximal inboard mounting arm and the second proximal outboard mounting arm.

5. The flexible catheter tip of claim 4, wherein the plurality of interlocking tabs longitudinally alternate between:
   the first proximal inboard mounting arm and the first proximal outboard mounting arm and
   the second proximal inboard mounting arm and the second proximal outboard mounting arm.

6. The flexible catheter tip of claim 1, wherein a distal end of the inboard understructure is connected to a distal end of the outboard understructure with a distal coupler.

7. The flexible catheter tip of claim 1, wherein the inboard understructure and the outboard understructure are formed from nitinol.

8. An integrated electrode structure comprising:
   a catheter shaft comprising a proximal end and a distal end, the catheter shaft defining a catheter shaft longitudinal axis;
   a flexible tip portion located adjacent to the distal end of the catheter shaft, the flexible tip portion comprising a flexible framework that includes:

an inboard understructure, the inboard understructure including a first continuous element that includes a first rectangular cross-section that extends generally parallel to the catheter shaft longitudinal axis;

an outboard understructure, the outboard understructure including a second continuous element that includes a second rectangular cross-section that extends generally parallel to the shaft longitudinal axis, wherein a proximal inboard portion of the inboard frame understructure and a proximal outboard portion of the outboard frame understructure each include a frame lock portion, each one of the frame lock portions being configured to interlock with one another; and a distal coupler that connects a distal end of the inboard understructure and a distal end of the outboard understructure.

9. The integrated electrode structure of claim 8, wherein the frame lock portion includes a tongue and groove structure.

10. The integrated electrode structure of claim 8, wherein a plurality of electrodes are disposed on the inboard understructure and the outboard understructure.

11. A medical device, comprising:

a catheter shaft comprising a proximal end and a distal end, the catheter shaft defining a catheter shaft longitudinal axis;

a flexible tip portion, the flexible tip portion comprising a flexible framework that includes:

an inboard understructure, the inboard understructure including a pair of proximal inboard mounting arms mounted in the distal end of the catheter shaft, wherein each of the proximal inboard mounting arms include an inboard frame lock portion; and an outboard understructure, the outboard understructure including a pair of proximal outboard mounting arms mounted in the distal end of the catheter shaft, wherein each of the proximal outboard mounting arms include an outboard frame lock portion that corresponds with the inboard frame lock portion, and wherein the outboard frame lock portion is configured to interlock with the inboard frame lock portion.

12. The medical device of claim 11, wherein the inboard understructure includes:

a pair of inboard arms that distally extend from the pair of proximal inboard mounting arms; and a flared head portion connected to distal ends of the pair of inboard arms.

13. The medical device of claim 12, wherein the outboard understructure includes:

a pair of outboard arms that distally extend from the pair of proximal outboard mounting arms; and a head portion connected to distal ends of the pair of outboard arms.

14. The medical device of claim 13, wherein the flared head portion and the head portion are connected via a distal coupler.

15. The medical device of claim 13, wherein:

a longitudinal width of the understructure that forms the head portion is less than a lateral width of the understructure that forms each one of the outboard arms; and a longitudinal width of the understructure that forms the flared head portion is less than a lateral width of each of the understructure that forms each of the inboard arms.

* * * * *